(12) United States Patent
Schnitzer et al.

(10) Patent No.: US 7,307,774 B1
(45) Date of Patent: Dec. 11, 2007

(54) MICRO-OPTICAL ANALYSIS SYSTEM AND APPROACH THEREFOR

(75) Inventors: Mark Jacob Schnitzer, Palo Alto, CA (US); Erik Paul Anderson, Stanford, CA (US); Eric David Cocker, Menlo Park, CA (US); Juergen Claus Jung, Palo Alto, CA (US); Benjamin A. Flusberg, Stanford, CA (US)

(73) Assignee: The Board of Trustees of the Leland Standford Junior University, Palo Alto, CA (US)

( * ) Notice: Subject to any disclaimer, the term of this patent is extended or adjusted under 35 U.S.C. 154(b) by 0 days.

(21) Appl. No.: 11/338,592

(22) Filed: Jan. 24, 2006

Related U.S. Application Data

(60) Provisional application No. 60/646,858, filed on Jan. 24, 2005, provisional application No. 60/646,711, filed on Jan. 24, 2005.

(51) Int. Cl.
*G02B 26/00* (2006.01)
*G02B 26/08* (2006.01)
(52) U.S. Cl. .................. 359/290; 359/198; 359/298
(58) Field of Classification Search ........... 359/198, 359/214, 224, 225, 290, 298
See application file for complete search history.

(56) References Cited

U.S. PATENT DOCUMENTS

| | | | |
|---|---|---|---|
| 5,201,318 A | 4/1993 | Rava et al. | |
| 5,345,941 A | 9/1994 | Rava et al. | |
| 5,419,323 A | 5/1995 | Kittrell et al. | |
| 5,421,337 A | 6/1995 | Richards-Kortum | |
| 5,421,339 A | 6/1995 | Ramanujam et al. | |
| 5,562,100 A | 10/1996 | Kittrell et al. | |
| 5,612,540 A | 3/1997 | Richards-Kortum | |
| 5,623,932 A | 4/1997 | Ramanujam et al. | |
| 5,697,373 A | 12/1997 | Richards-Kortum | |
| 5,699,795 A | 12/1997 | Richards-Kortum | |
| 5,842,995 A | 12/1998 | Mahadevan-Jansen | |
| 5,920,399 A | 7/1999 | Sandison et al. | |
| 5,929,985 A | 7/1999 | Sandison et al. | |
| 5,991,653 A | 11/1999 | Richards-Kortum | |
| 6,007,208 A | 12/1999 | Dickensheets et al. | |
| 6,095,982 A | 8/2000 | Richards-Kortum | |
| 6,135,965 A | 10/2000 | Turner et al. | |

(Continued)

OTHER PUBLICATIONS

Thomas D. Wang et al. "Confocal fluorescence microscope with dual-axis architecture and biaxial postobjective scanning." Jul./Aug. 2004. *Journal of biomedical Optics*. vol. 9 No. 4:735-742.

*Primary Examiner*—Ricky Mack
*Assistant Examiner*—William C Choi
(74) *Attorney, Agent, or Firm*—Crawford Maunu PLLC

(57) ABSTRACT

Imaging, testing and/or analysis of subjects is facilitated with a micro-mirror-based access approach. According to an example embodiment, a micro-mirror is implemented to direct light to a live being such as a biological specimen or a living being. Light from the live being is detected and implemented for use in analyzing the live being. In certain applications, the micro-mirror is fastened to a live being, such as to a skull of a live mouse, while the live being is allowed to move in an unanesthetized state. Behavior of the live being and detected response from the live being are concurrently used to analyze the live being.

27 Claims, 9 Drawing Sheets

U.S. PATENT DOCUMENTS

| | | |
|---|---|---|
| 6,187,289 B1 | 2/2001 | Richards-Kortum |
| 6,241,662 B1 | 6/2001 | Richards-Kortum |
| 6,258,576 B1 | 7/2001 | Richards-Kortum |
| 6,370,422 B1 | 4/2002 | Richards-Kortum |
| 6,423,956 B1 | 7/2002 | Mandella et al. |
| 6,483,641 B1 * | 11/2002 | MacAulay ................ 359/385 |
| 6,485,413 B1 | 11/2002 | Boppart et al. |
| 6,571,118 B1 | 5/2003 | Utzinger et al. |
| 6,580,941 B2 | 6/2003 | Webb |
| 6,593,101 B2 | 7/2003 | Richards-Kortum |
| 6,639,674 B2 | 10/2003 | Sokolov et al. |
| 6,697,666 B1 | 2/2004 | Richards-Kortum |
| 6,766,184 B2 | 7/2004 | Utzinger et al. |
| 2002/0065468 A1 | 5/2002 | Utzinger et al. |
| 2002/0080359 A1 | 6/2002 | Denk et al. |
| 2002/0110590 A1 | 8/2002 | Shaked et al. |
| 2002/0127632 A1 | 9/2002 | Richards-Kortum |
| 2002/0135752 A1 | 9/2002 | Sokolov et al. |
| 2002/0141714 A1 | 10/2002 | Reed et al. |
| 2002/0146202 A1 | 10/2002 | Reed et al. |
| 2003/0031410 A1 | 2/2003 | Schnitzer |
| 2003/0103262 A1 | 6/2003 | Descour et al. |
| 2003/0117715 A1 | 6/2003 | Schnitzer |
| 2003/0118305 A1 | 6/2003 | Reed et al. |
| 2003/0142934 A1 | 7/2003 | Pan et al. |
| 2004/0023415 A1 | 2/2004 | Sokolov et al. |
| 2004/0064053 A1 | 4/2004 | Chang et al. |
| 2004/0143190 A1 | 7/2004 | Schnitzer |
| 2004/0162489 A1 | 8/2004 | Richards-Kortum |
| 2004/0260148 A1 | 12/2004 | Schnitzer |
| 2005/0080343 A1 | 4/2005 | Richards-Kortum |
| 2005/0157981 A1 | 7/2005 | Berier et al. |
| 2005/0207668 A1 | 9/2005 | Perchant et al. |
| 2005/0242298 A1 | 11/2005 | Genet et al. |

* cited by examiner

MICRO-OPTICAL ANALYSIS SYSTEM AND APPROACH THEREFOR

RELATED PATENT DOCUMENTS

This patent document claims the benefit, under 35 U.S.C. §119(e), of U.S. Provisional Patent Application No. 60/646,858, entitled "Optical Analysis Systems and Approaches" and filed on Jan. 24, 2005; this patent document further claims the benefit, under 35 U.S.C. §119(e), of U.S. Provisional Patent Application No. 60/646,711, entitled "Live Being Optical Analysis System and Approach" and filed on Jan. 24, 2005.

FEDERALLY-SPONSORED RESEARCH AND DEVELOPMENT

This invention was made with Government Support under contract 0352456 awarded by the National Science Foundation, and contract N00014-04-1-0826 awarded by the Department of the Navy. The U.S. Government has certain rights in this invention.

FIELD OF THE INVENTION

The present invention relates generally to optical analysis, and more particularly to analysis approaches involving the optical analysis of subjects using small-scale optics, such as those involving micro-electro-mechanical systems (MEMS).

BACKGROUND

A variety of approaches to optical imaging and analysis have been used for many different applications. For example, the endoscope is a useful tool for a variety of applications such as biological research, medical diagnostics, and for image guidance in surgical procedures. Conventional endoscopes utilize a white light source to illuminate a sample and reflected light to visualize the same sample. Such conventional endoscopes are typically limited, however, to visualizing the surface of a sample or to surface inspection within a hollow tissue cavity.

Certain types of optical analysis approaches are discussed in connection with the following patent documents: U.S. Pat. Nos. 6,485,413 and 6,423,956, and U.S. Patent Application Publication Number US 2003/0142934.

Many applications for which optical analysis would be beneficial are subject to a variety of limitations to such analysis. For example, space constraints in many applications limit the use of certain tools that are not generally scaleable in a manner that would facilitate such tools' use for these applications. In addition, while certain tools have been useful in applications characterized by small space constraints, these tools are often limited in their ability to achieve desirable results, or by their ability for use with certain samples such as biological samples that may include live beings. Furthermore, many optical analysis approaches are limited to the analysis of linear optics.

Some applications benefit from subcutaneous analysis, in particular with a specimen. However, invasive analysis of a specimen can be challenging, particularly when the analysis is to be made over time. For example, when a subcutaneous area of a living specimen is to be accessed multiple times, processes used to facilitate the access must be repeated. In addition, each time a specimen is accessed subcutaneously, infection and other medical complications can arise.

The above and other issues have presented challenges to optical analysis approaches and, in particular, to optical imaging in applications exhibiting relatively small space such as for endoscopic and microscopic applications.

SUMMARY OF THE INVENTION

The present invention is directed to overcoming the above-mentioned challenges and others related to the types of devices and applications discussed above and in other applications. These and other aspects of the present invention are exemplified in a number of illustrated implementations and applications, some of which are shown in the figures and characterized in the claims section that follows.

According to an example embodiment, an optical system is adapted for analyzing a sample. The system includes a light source, a light direction arrangement and a light detector. The light direction arrangement is attached to a live being (e.g., via screws or other fasteners), and includes a micro-mirror, an actuator and a dichroic device. The actuator controllably moves the micro-mirror to direct light from the light source to different target locations of the sample. The dichroic device directs source light to the sample and directs light from the sample to the light detector. The light detector is configured and arranged to receive light from the sample, via the dichroic device, and to present a signal characterizing the detected light.

In another example embodiment, the light direction arrangement is fastened to tissue of a live being to maintain the micro-mirror in a position relative to the live being while the live being is allowed to move freely (e.g., to move about in a cage or room, or in a natural environment). The actuator controllably moves the micro-mirror to direct light to different target locations of the live being while the live being moves in an unanesthetized state.

According to another example embodiment of the present invention, a live being is analyzed using a light-direction arrangement fastened thereto. The light direction arrangement includes a micro-mirror, an actuator for controllably moving the micro-mirror to direct light from the light source to different target locations of the sample, and a dichroic device that directs light from the sample to a light detector. The live being is allowed to move freely with the light direction arrangement fastened thereto. While the live being is allowed to move freely, light is directed to the micro-mirror arrangement and a voltage is applied to the actuator to cause the micro-mirror to oscillate. The oscillation of the micro-mirror facilitates the scanning of light across a target portion of the subcutaneous tissue of the live being via the dichroic device. The dichroic device directs an optical response of the subcutaneous tissue to the light detector, which detects and uses the light to analyze the live being. In some applications, the timing of the detected response is correlated to a common time during which an external behavioral response is detected.

The above summary is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings in which.

Figure 1A:
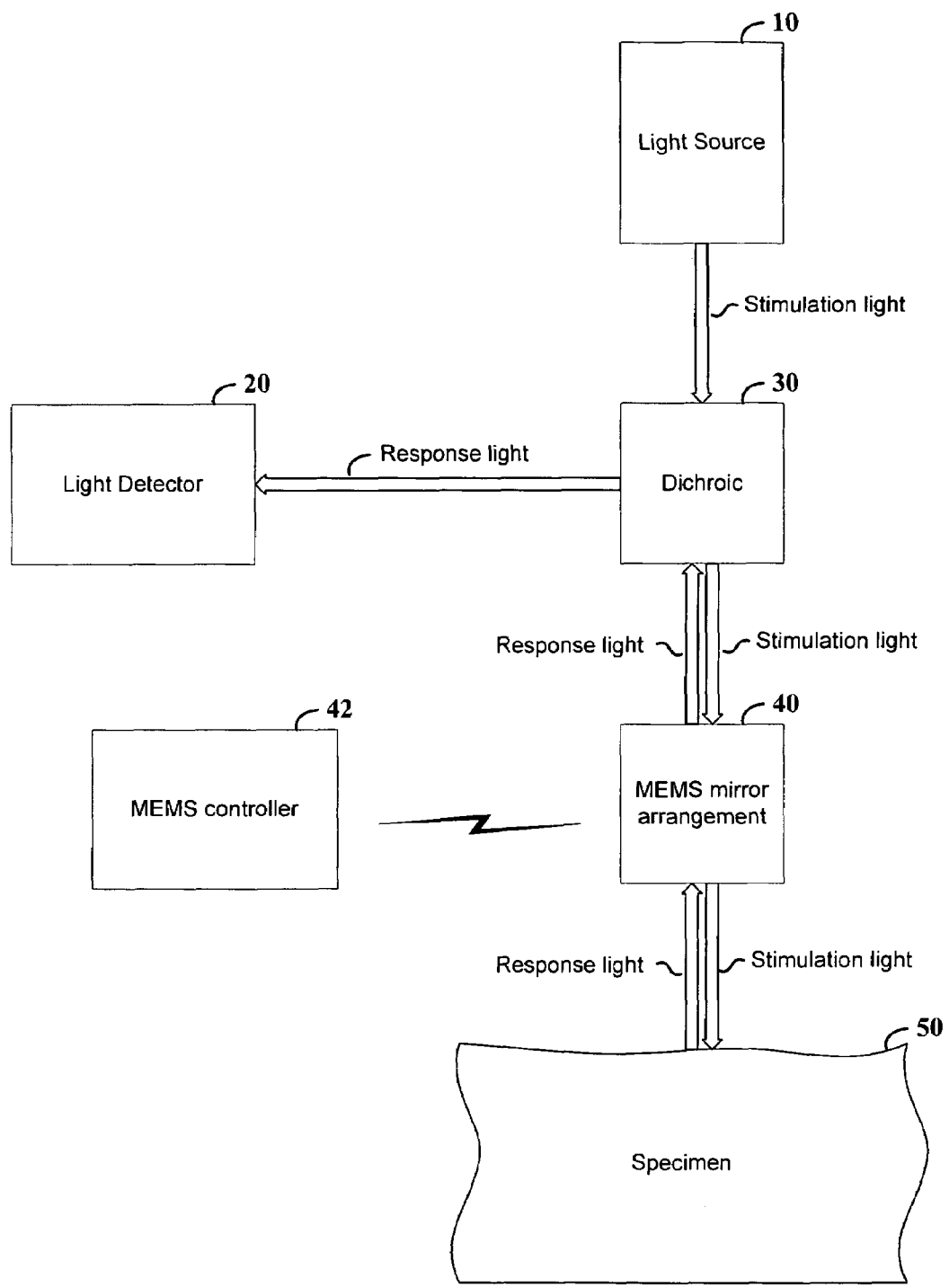
FIG. 1A shows an optical analysis approach, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and approaches, and the invention has been found to be particularly suited for approaches to optical analysis involving the scanning of a specimen via relatively small-scale scanning mechanism. While the present invention is not necessarily limited to such applications, various aspects of the invention may be appreciated through a discussion of various examples using this context.

According to an example embodiment of the present invention, an approach to optical analysis involves the use of a micro-mirror arrangement, including one or more mirrors, integrated with a light directing arrangement to facilitate optical stimulation and response detection with a sample such as a biological specimen. The micro-mirror arrangement is used to direct light to the sample, with light from the sample being collected and used for analyzing the sample (i.e., detecting a response, or condition, of the sample). The micro-mirror arrangement is selectively implemented in relatively small areas, facilitating near-target placement of the micro-mirror arrangement.

In some applications, the micro-mirror arrangement includes a MEMS (micro-electro-mechanical systems) mirror, and the optical analysis approach therewith involves the optical stimulation of a sample to generate nonlinear optical responses. Certain approaches are thus implemented to facilitate the detection of a nonlinear response. For example, certain stimulation approaches known to generate nonlinear optical responses are used in connection with a sample and the scanning of the sample with the MEMS mirror. Detected nonlinear optical responses to the scanning are made available for use in analyzing the sample.

In certain implementations, arrangements with which the MEMS mirror is used direct response light of a wavelength different than that of stimulation light to facilitate the detection and analysis of the response light (i.e., by analyzing light of an appropriate wavelength for the response light, mitigating interference from reflected stimulation light). In one application, a light detector and/or a light director (e.g., a mirror and/or another object that directs light) is implemented to analyze wavelength-related characteristics of a response of the sample. For instance, where light of a particular wavelength is directed to the sample via a MEMS mirror, light of a different wavelength is collected from the sample as a response, and analyzed accordingly. Certain characteristics of a light collector (or detector) are selectively tailored to facilitate the detection of light at such a different wavelength. Some applications involve the use of a wavelength-dependent dichroic element, such as a beam splitter, that directs light of a particular wavelength (e.g., the wavelength of light related to a response of the sample) to a detector.

In another example embodiment of the present invention, a light director is adapted for analyzing a sample using a movable micro-mirror and a dichroic device to selectively pass stimulation and response light. The micro-mirror is moved using an actuator, such as a pivoting or translating actuator, for controllably moving the mirror to direct light from a light source, such as a laser or incandescent source, to different target locations on the sample. The dichroic device includes one or more wavelength-selective components, such as a beam splitting prism, a dichroic mirror or a curved dichroic beam splitter. Such a dichroic device is selectively placed in an implantable capillary-type arrangement, where appropriate, for selective wavelength-dependent direction of light into and/or from a sample. In some applications, the dichroic device (e.g., as shown below in FIG. 1A) is used to separate wavelengths that are subsequently used to generate a multi-channel image.

According to another example embodiment of the present invention, an optical system is adapted for analyzing a sample. The system includes a light source, a light director, an implantable capillary-type arrangement, a dichroic device and a light detector. The light director includes a micro-mirror, an actuator and a dichroic device. The actuator (e.g., a comb actuator) is adapted to controllably move the micro-mirror, such as by pivoting the micro-mirror about one or more axes. In some applications, more than one actuator is used, such as one for pivoting the micro-mirror in a first direction and another for pivoting the micro-mirror in a second direction, or for moving the micro-mirror laterally and/or vertically relative to the sample. Using an actuator or actuators, the micro-mirror is controllably moved to direct light from the light source to different target locations on the sample. In some applications, an actuator is adapted to move the micro-mirror in a manner that causes light to scan across a target area in the sample.

The dichroic device is adapted to pass light from the light source to the sample and to direct response light from the sample to a light detector, with wavelength-dependant characteristics of the dichroic device facilitating the selective direction of the response light to the light detector. The dichroic device may be implemented using one or more of a variety of approaches, such as those involving a beam splitter or other wavelength-selective component as discussed herein.

The light detector is configured and arranged to receive light from the sample, via the capillary-type arrangement and the dichroic device, and to present a signal characterizing the detected light. The light detector is implemented using one or more of a variety of devices, such as a photo detector, light collector, photo multiplier tube, imaging electronics, lenses and others as discussed, e.g., in connection with other embodiments and implementations herein.

In one example embodiment, a MEMS-based light direction arrangement as discussed above (and elsewhere herein) is implemented for long-term analysis of live beings in a freely-moving state. The MEMS-based light direction arrangement includes a MEMS micro-mirror and actuator adapted to direct light into a sample for analysis thereof, and to pass light (e.g., response light) from the sample to a detector. The MEMS-based light direction arrangement is mounted to a live being using screws, stitches or other mechanical-type fasteners such as may be known in the medical arts, and is left in-place over a period of hours, days or longer. During this period, the live being is generally in an un-anesthetized state and able to move about while the MEMS-based light direction arrangement is attached thereto. In this regard, various applications are directed to approaches wherein the MEMS-based light direction arrangement is implemented in a lightweight form, facilitated by the small size of the micro-mirror, actuator and other components, in many applications less than about 5 grams, and in some applications, less than about 3 grams.

For instance, certain applications are directed to the analysis of freely-moving mice, with the MEMS-based light direction arrangement affixed to the head of a mouse and adapted to scan light into the mouse's brain to stimulate and detect a response therefrom. The fixable nature and relatively light weight of the MEMS-based light direction arrangement facilitates such analysis without necessarily requiring that the mouse be anesthetized. Furthermore, this approach facilitates the study of mice under conditions that may involve treatment (e.g., drugs) or other long-term analysis approach that benefits from the mice being in an active (freely-moving) state. For general information regarding the analysis of live animals and for specific information regarding approaches to the analysis of mice and other live animals to which various example embodiments discussed herein are directed, reference may be made to U.S. patent application Ser. No. 11/338,598 entitled "Live Being Optical Analysis System and Approach" and filed on Jan. 24, 2006, which is fully incorporated herein by reference.

In some applications, the MEMS-based light direction arrangement is used to analyze relationships between subject behavior and cellular properties in the live being undergoing analysis. For instance, affixing the MEMS-based light direction arrangement to the skull of a mouse, while allowing the mouse to move freely, facilitates the observation of subcutaneous tissue characteristics such as cellular properties in the mouse while also observing the physical movement and behavior of the mouse. In this regard, various implementations of the MEMS-based light direction arrangement are directed to analysis approaches involving the observation of both internal properties of a live being, as stimulated and detected via the MEMS-based light direction arrangement, and external physical behavior of the live being.

In another example embodiment of the present invention, a MEMS arrangement is implemented with an optical analysis capillary-type approach to facilitate the optical analysis of a sample such as a biological specimen or a living being. A capillary is configured for accepting an optical probe, such as an endoscopic probe via an open end of the capillary, with a closed end of the capillary facilitating the passage of light between the specimen and the probe. A portion of the capillary including the closed end thereof is implanted into a sample, with the open end accessible for insertion of an optical probe. A MEMS mirror arrangement as discussed herein is implemented with the capillary in scanning light via the closed end of the capillary. In some applications, the MEMS mirror arrangement is implemented inside the capillary.

In other example embodiments, the capillary includes optical devices such as lenses, filters, polarizers or other devices that facilitate the passage of light between a probe and a sample. In certain example embodiments, the capillary is implemented with a cover slip, or sheath, that facilitates implantation into a specimen. In another example embodiment, at least some of the capillary is coated or otherwise configured with material that inhibits certain adverse characteristics of invasive implantation into live beings.

In some instances, an optical probe implemented with one or more of the approaches described herein is a microendoscope probe, such as those based on GRIN lenses. Various example embodiments are directed to the user of GRIN lens applications similar to those described in the following U.S. Patent Publications, each of which lists Mark Schnitzer as an inventor thereof: No. 20040260148 entitled "Multi-photon endoscopic imaging system"; No. 20040143190 entitled "Mapping neural and muscular electrical activity"; No. 20030118305 entitled "Grin fiber lenses"; No. 20030117715 entitled "Graded-index lens microscopes"; No. 20030031410 entitled "Multi-photon endoscopy"; No. 20020146202 entitled "GRIN fiber lenses"; and No. 20020141714 entitled "Grin-fiber lens based optical endoscopes"; all of which are fully incorporated herein by reference.

In other particular instances, an optical probe implemented with one or more of the approaches described herein includes optical fibers, and in some applications, a bundle of optical fibers. Various example embodiments are directed to the use of optical fibers such as those described in the following U.S. Patent Publications: No. 20050157981 entitled "Miniaturized focusing optical head in particular for endoscope" (to Berier et al.), No. 20050207668 entitled "Method for processing an image acquired through a guide consisting of a plurality of optical fibers" (to Perchant, et al.), No. 20050242298 entitled "Method and equipment for fiber optic high-resolution, in particular confocal, fluorescence imaging" (to Genet, et al.) and No. 20030103262 entitled "Multimodal miniature microscope" (to Richards-Kortum, et al.); and as those described in the following U.S. Pat. Nos. 6,766,184 (Utzinger, et al.) entitled "Methods and apparatus for diagnostic multispectral digital imaging," No. 6,639,674 (Sokolov, et al.) entitled "Methods and apparatus for polarized reflectance spectroscopy," No. 6,571,118 (Utzinger et al.) entitled "Combined fluorescence and reflectance spectroscopy," and No. 5,929,985 (Sandison, et al.) entitled "Multispectral imaging probe," all of which are fully incorporated herein by reference.

FIG. 1A shows an optical analysis approach, according to another example embodiment of the present invention. Stimulation light from a light source 10 is passed via a dichroic device 30, such as a beam splitter, to a MEMS mirror arrangement 40 that is controlled via a MEMS controller 42 that applies voltage and/or other controls to control movement of the MEMS mirror arrangement. While shown separately, the MEMS controller 42 may be included with the MEMS mirror arrangement 40, and further may be implemented using, for example, a computer processor programmed to supply a control output and, where appropriate, other devices to appropriately use the control output to control the MEMS mirror arrangement. The MEMS mirror arrangement 40 scans the stimulation light to a target portion of a specimen 50, such as a living being. The scanned stimulation light generates a response in the specimen 50, with response light passing back through the MEMS mirror arrangement and to the dichroic device 30. The response light is then passed to a light detector by the dichroic device 30. The dichroic device 30 may, for example, implement a wavelength-dependent component that directs response light, of a different wavelength than the stimulation light, to the light detector 20. In some applications, the stimulation light is implemented to generate a nonlinear optical response in the specimen 50, with light associated with this nonlinear optical response being passed to the light detector 20 and used to analyze the specimen.

Figure 1B:
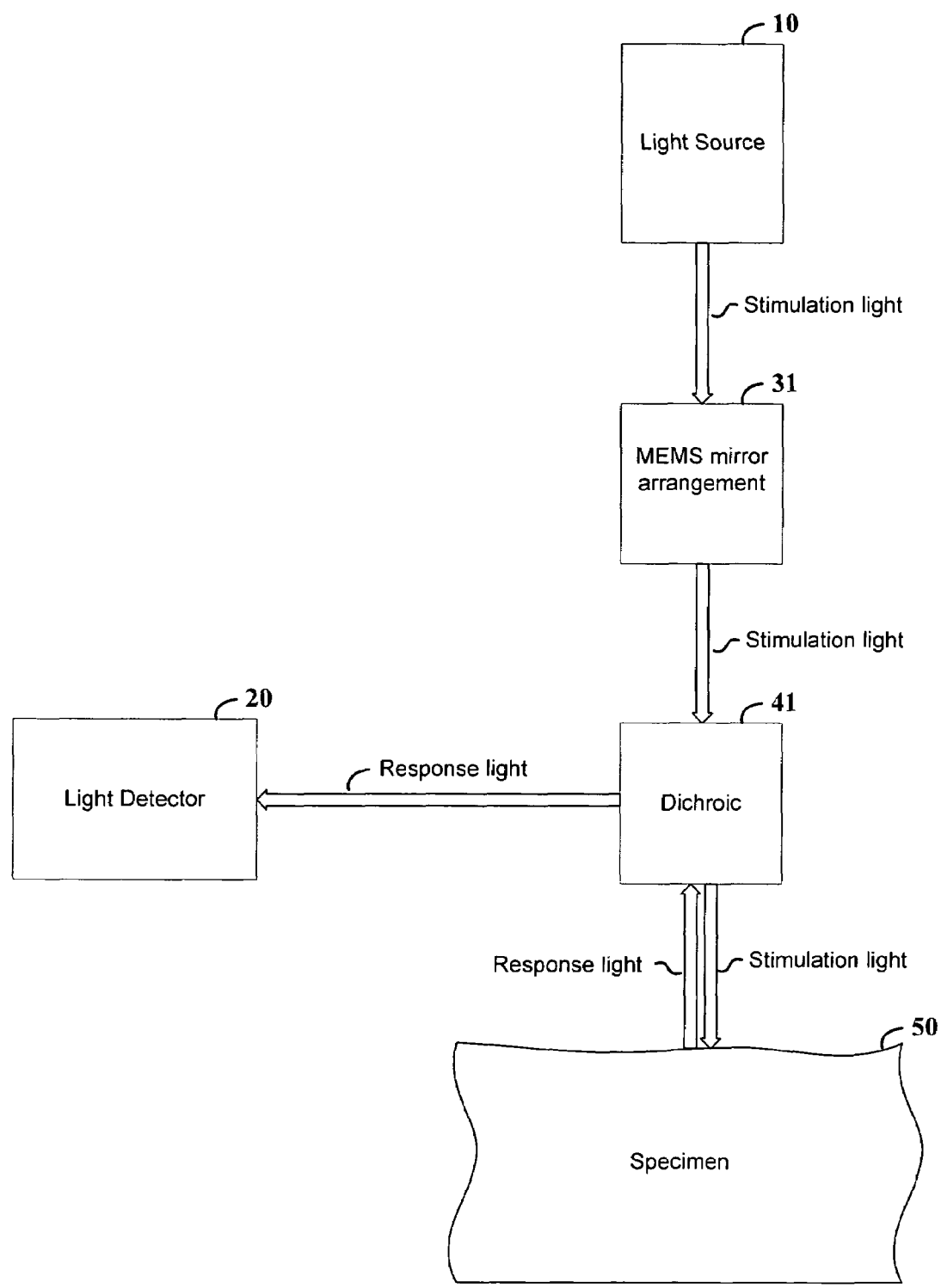
FIG. 1B shows an optical analysis approach, according to another example embodiment of the present invention.

FIG. 1B shows an optical analysis approach, according to another example embodiment of the present invention. The approach shown in FIG. 1B is similar to that shown in FIG. 1A, with the light source 10, light detector 20 and specimen 50 having similar reference numbers. In this application, a MEMS mirror arrangement 31 is placed before a dichroic device 41, relative to the light source 10. In this regard, stimulation light from the light source 10 is passed to the MEMS mirror arrangement 31, which scans the stimulation light into the specimen 50, via the dichroic device 41. Response light from the specimen, generated in response to the stimulation light scanned with the MEMS mirror arrangement 31, is passed from the dichroic 41 to the light detector 20. As with the example shown in FIG. 1A and discussed above, the stimulation light can be implemented for the generation of a nonlinear optical response in the specimen 50.

Figure 2:
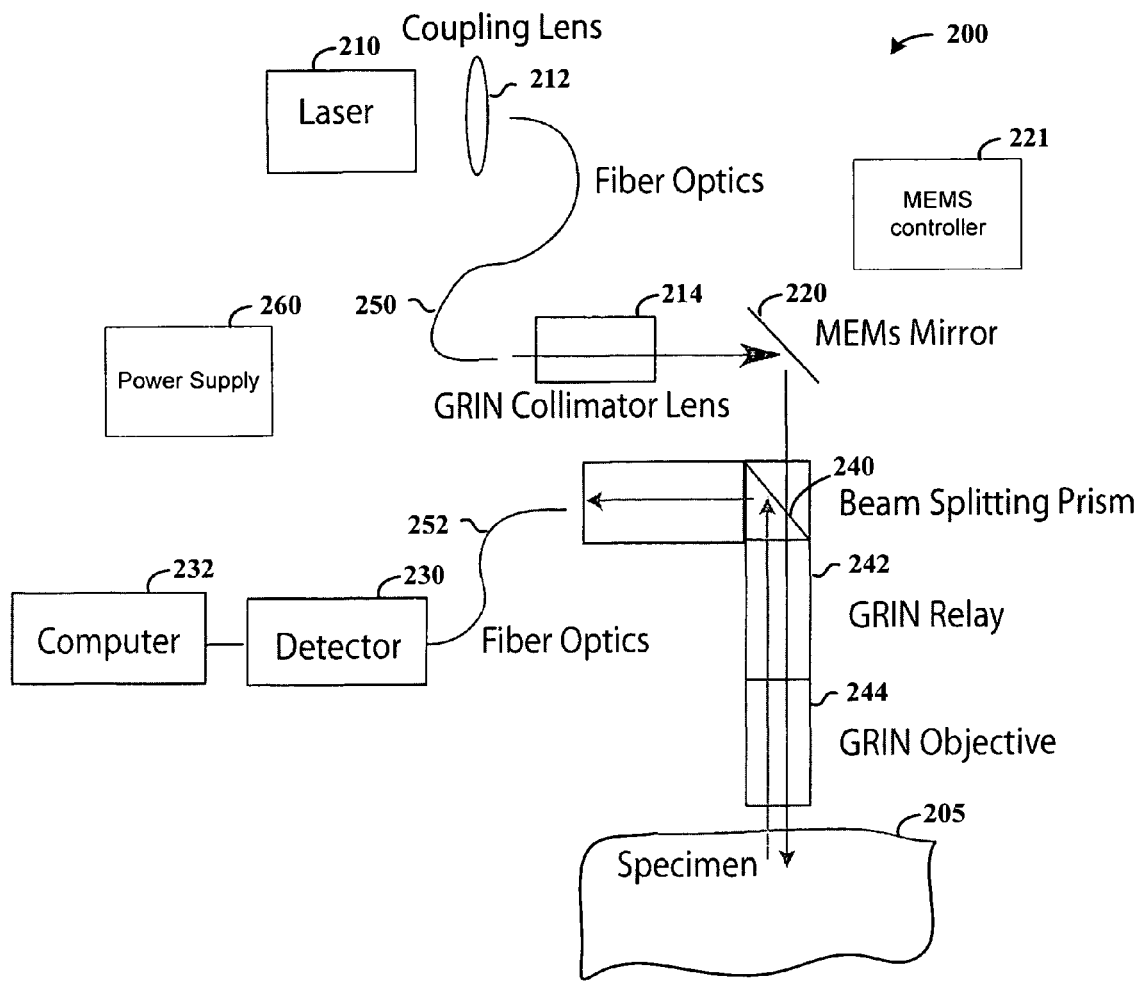
FIG. 2 shows a system for optical imaging, according to another example embodiment of the present invention.
Figure 3A:
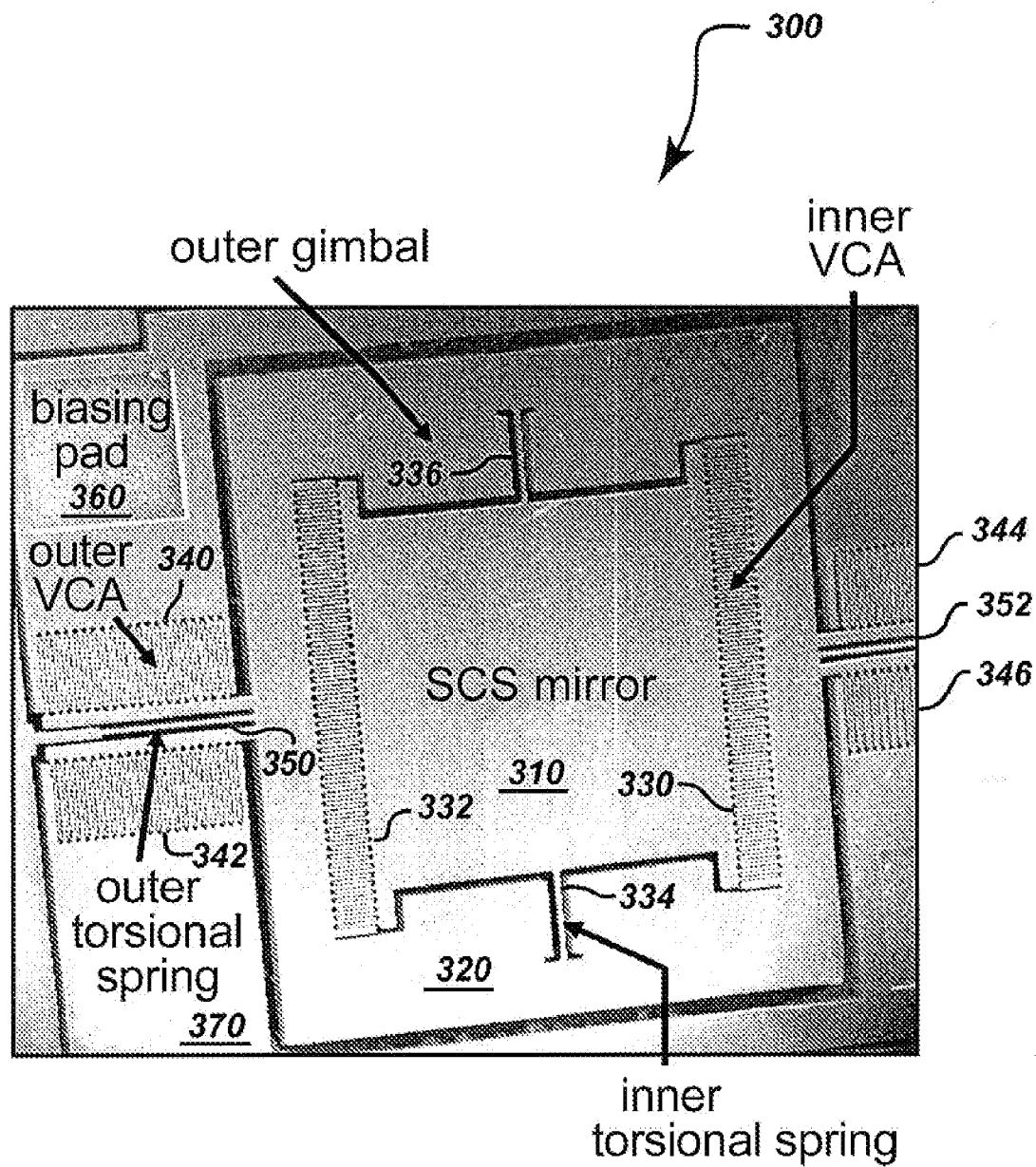
FIG. 3A shows a MEMS arrangement, according to another example embodiment of the present invention.
Figure 3B:
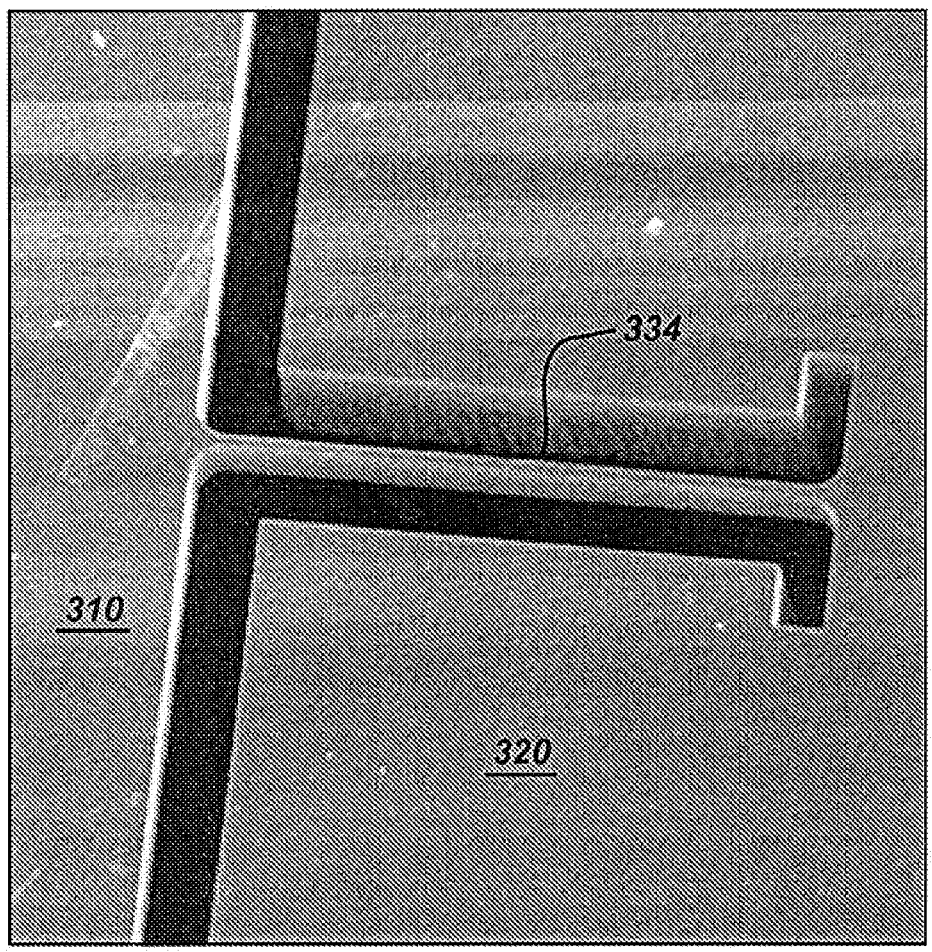
FIG. 3B shows an inner torsional spring of the MEMS arrangement shown in FIG. 3A, according to another example embodiment of the present invention.
Figure 3C:
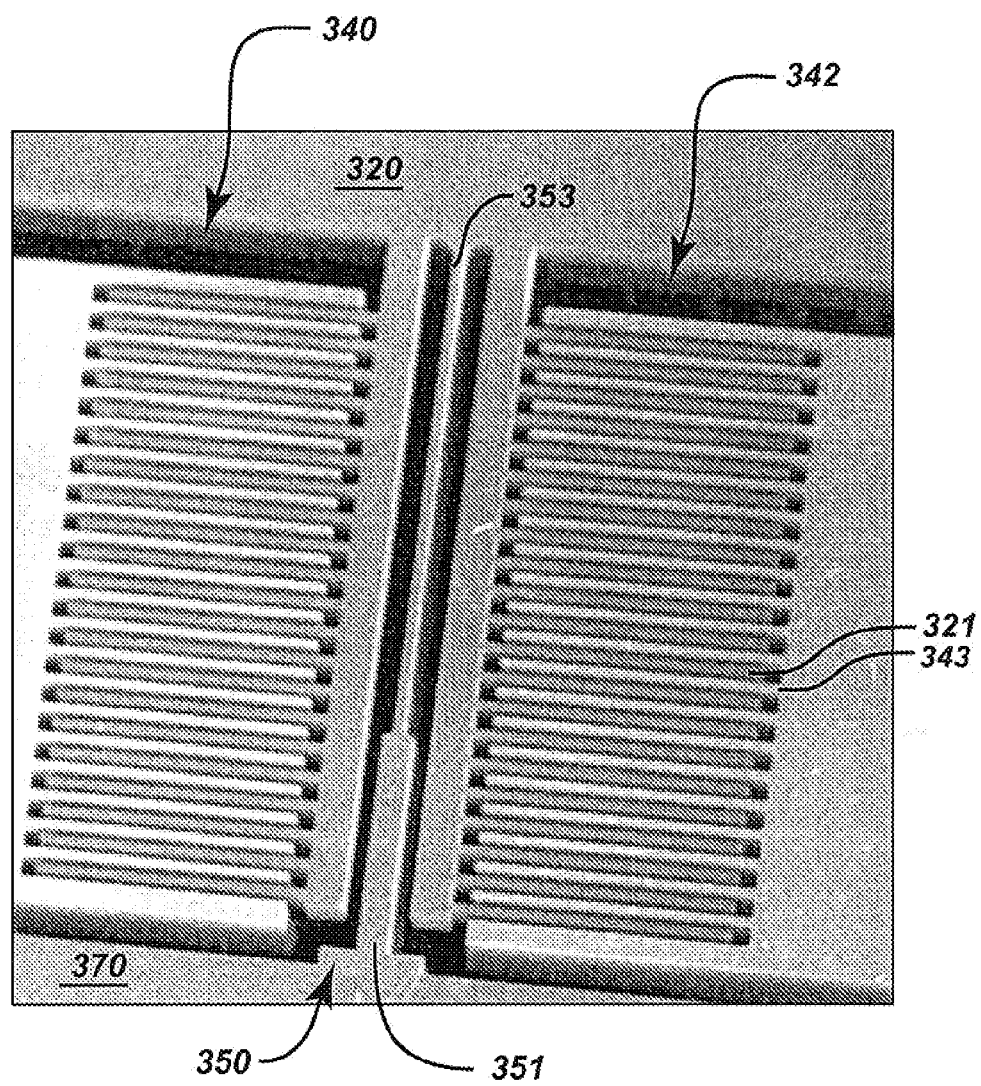
FIG. 3C shows a vertical comb actuator (VCA) bank of the MEMS arrangement shown in FIG. 3A, according to another example embodiment of the present invention.

FIG. 2 shows an optical analysis system 200, according to another example embodiment of the present invention. The optical analysis system 200 includes a light source 210 and a MEMS mirror 220 adapted for actuation (e.g., tilting in at least one-dimension) to selectively direct the light from the light source to a target location or locations on a sample 205 (e.g., a specimen). A MEMS controller 221 controls the MEMS mirror 220, for example by applying a selected voltage to an actuating portion of the MEMS mirror. Examples of MEMS mirrors (or mirror arrangements) that can be implemented with the MEMS mirror 220 are shown in FIGS. 3A-3C.

Target locations may include, for example, locations of interest for a particular type of analysis or specific locations relating to implanted devices, such as probes, that facilitate the detection of a response from the sample. A light conduit such as a fiber optic conduit 250 transports light from the laser 210, coupled by a coupling lens 212, to a gradient refractive index (GRIN) optical arrangement 214 that collimates the light onto the MEMS mirror 220. A dichroic device 240, such as a dichroic beams splitter and/or prism type beam splitter, is located in the light path between the MEMS mirror 220 and the sample 205. A GRIN relay lens 242 is located between the dichroic device 240 and the sample 205, and a GRIN objective lens 244 is located between the GRIN relay lens and the sample. The MEMS 220 thus directs light from the light source 210 to the sample 205, via the dichroic device 240, GRIN relay 242 and GRIN objective lens 244.

Light from the sample 205 (e.g., reflected or refracted light), is focused by a GRIN lens (e.g., the GRIN objective lens 244) and passed by the dichroic device 240 to a detector 230 via a light conduit 252 such as a fiber optic conduit. The detector 230 may, for example, include a photo-multiplier tube (PMT) or any arrangement that can process light to generate an output that can be used to characterize the light from the sample. In some implementations, a computer 232 or other device is used to characterize the light in such a manner.

Mirrors that can be implemented in connection with FIG. 2 (in connection with and/or alternative to the MEMS mirror) include a variety of structures and implement a variety of approaches, depending upon the particular application. In one example, a MEMS mirror is micro-machined from a silicon substrate using metals and lithographic techniques that are standard in the electronics industry. Further, the placement of the MEMS mirror is selected to meet certain application-specific criteria. For example, while shown in FIG. 2 between the dichroic device and the light source, the MEMS mirror is optionally located in other arrangements, such as between the beam splitter and the sample. In such an approach, the dichroic device can be removed from any miniaturized portions of the arrangement, such as may facilitate insertion into very small locations as may be applicable, for example, with in vivo analysis.

In some applications, the GRIN collimator lens 214, MEMS mirror 220, the beam splitting prism, GRIN relay 242 and GRIN objective 244 are coupled in a common arrangement fastened to the specimen 205. Such an arrangement may be implemented, for example, in connection with the mount shown in FIG. 3D and discussed further below. This approach facilitates mounting, for example, to a freely-moving being such as a mouse.

In certain applications involving a mount and a common arrangement, the laser 210 and corresponding optics between the laser and the GRIN collimator lens 214 are also coupled in the aforesaid common arrangement. Similarly, the detector 230 may also be coupled to the aforesaid common arrangement, or both the laser 210 and detector may be coupled to the common arrangement. In this regard, the fiber optics 250 and 252 may selectively be omitted where appropriate (e.g., where the laser 210 is arranged adjacent to the micro-mirror 220, the fiber optics 250 may not be necessary. With these approaches, the system 200 can be primarily included in a common device that can be fastened to the specimen 205, with light and/or an electric signal passed to or from the arrangement to selectively control and/or gather information from the specimen. In certain applications involving the detector 230 mounted to the specimen, wireless signals are passed to the computer 232 to characterize detected light.

Figure 3D:
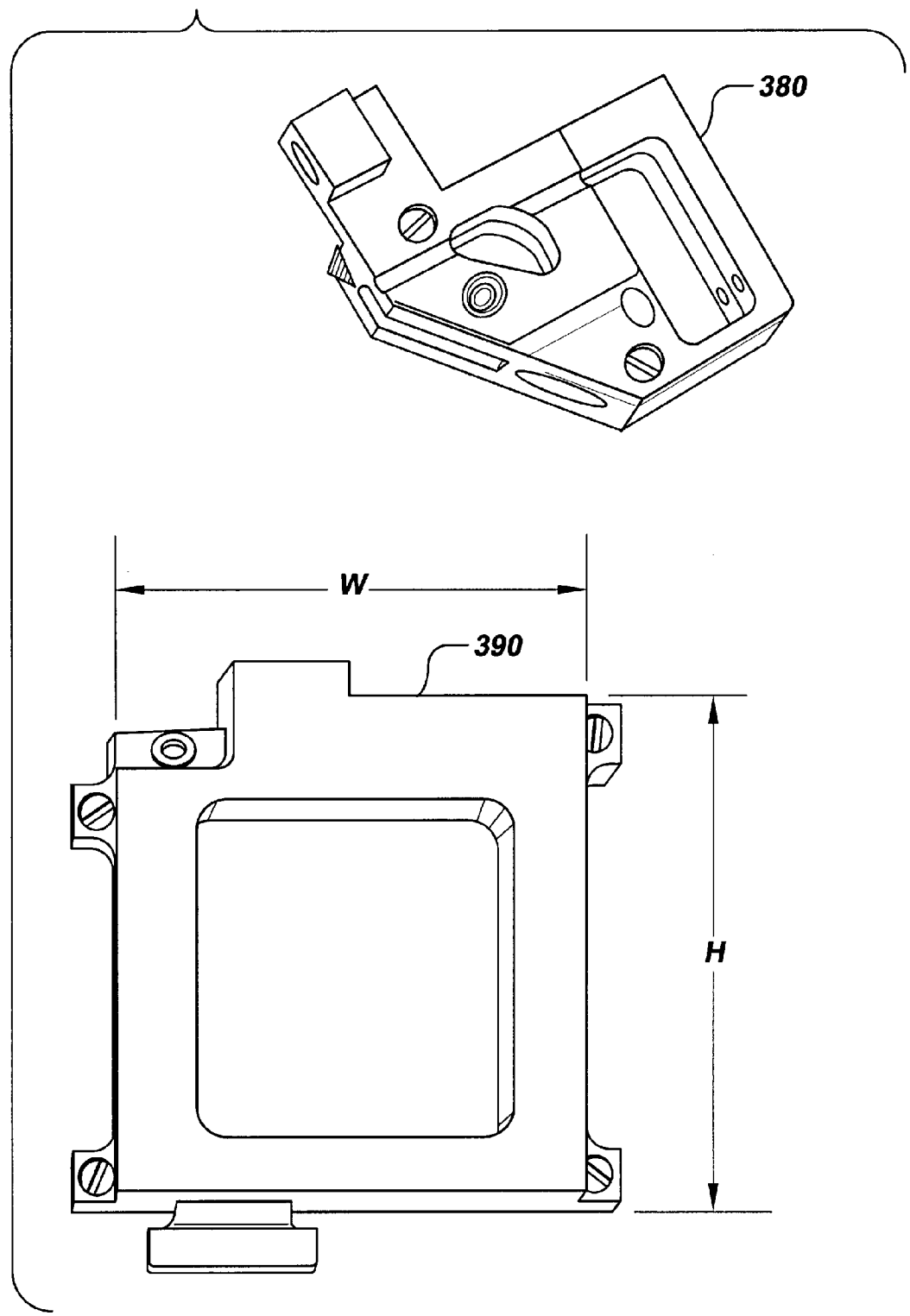
FIG. 3D shows a MEMS scan unit and mounting arrangement, according to another example embodiment of the present invention.

A power supply 260 is optionally coupled with the system 200 and, where mounted to a base as discussed above (e.g., as shown in FIG. 3D), is selectively mounted to the same base to provide power at a location on the specimen 205. For example, the power supply 260 may supply power to some or all of the MEMS controller 221, laser 210 and detector 230. In this regard, the mobility of the system 200 is selectively increased by providing an ability to operate the system 200 in a manner that is relatively independent from power and/or light supply. When attached to a live being, the absence of connected lines can facilitate the movement of the live being. In this regard, other embodiments are further directed to inclusion of the computer 232 with the aforesaid common arrangement.

FIG. 3A shows a MEMS scanning arrangement 300, according to another example embodiment of the present invention. The arrangement 300 is selectively implemented with microscopy and/or microendoscopy approaches, such as two-photon microscopy. In some applications, these approaches are implemented using relatively fast-axis acquisition rates, with certain applications facilitating acquisition rates up to, for example, about 3.5 kHz. In this regard, the arrangement 300 can also be implemented in connection with one or more example embodiments described herein, such as with the arrangements shown in FIGS. 1A-2.

The arrangement 300 includes a MEMS scanning mirror 310, fabricated within a single-crystalline silicon (SCS) device layer (e.g., a double silicon-on-insulator (SOI) wafer fabricated using reactive ion etching). The MEMS scanning mirror 310 is coupled to an outer gimbal 320 via two inner torsional springs 334 and 336. The outer gimbal 320 is coupled to an outer base layer 370 via outer torsional springs 340, 342, 344 and 346. The MEMS scanning mirror 310 thus rotates along an axis along which inner torsional springs 334 and 336 lie, and further rotates along another axis, along which outer torsional springs 350 and 352 lie. While applicable to a variety of shapes and sizes, the arrangement 300 is amenable for manufacture with a die of about 3.2×3.0 mm in size, with a MEMS scanning mirror of about 760×760 µm.

Six banks of vertical comb actuators (VCAs) drive the MEMS scanning mirror 310, with each bank coupled to receive a bias voltage, such as via biasing pad 360 shown by way of example. Such a bias voltage may be supplied using, for example, a MEMS mirror controller 42 as shown in FIG. 1A and described above. These VCA banks include inner VCA banks 330 and 332, and outer VCA banks 340, 342, 344 and 346. Specifically, inner VCA banks 330 and 332 act to rotate the MEMS scanning mirror 310 about an axis along the torsional springs 334 and 336. Similarly, outer VCA banks 340 and 342 at torsional spring 350, and outer VCA banks 344 and 346 at torsional spring 352 act to rotate the MEMS scanning mirror 310 about an axis along the torsional springs 350 and 352. Biasing pad 360 is arranged to apply a biasing voltage to the outer VCA bank 340; additional biasing pads are thus selectively implemented with the other VCA banks as appropriate to effect application of such a biasing voltage and rotation of the MEMS scanning mirror 310. In addition, other approaches to biasing the VCA banks are selectively implemented in addition to and/or in the alternative of a biasing pad.

In some applications, one pair of outer VCA banks (340 and 342, or 344 and 346) is selectively omitted, with the remaining pair of torsional springs implemented to rotate the MEMS scanning mirror 310. In certain applications, a single VCA bank is used for rotating the MEMS scanning mirror 310 along one or both axes. As can be seen, a variety of approaches to rotating the MEMS scanning mirror 310 are selectively implemented with the MEMS arrangement 300.

The MEMS scanning mirror 310 is implemented with a variety of different shapes and characteristics, depending upon the application. For instance, in one example embodiment, the MEMS scanning mirror 310 has a radius of curvature that is over about 1 meter. Various other radii of curvature are selectively implemented for certain applications. The MEMS scanning mirror 310 is also selectively coated, such as with a metal coating, or uncoated. The surface roughness of the MEMS scanning mirror 310 is also tailored as appropriate for certain applications, and in one implementation exhibits an average surface roughness (Ra) of less than about 16 nanometers.

FIG. 3B shows an inner torsional spring 334 of the MEMS arrangement shown in FIG. 3A, according to another example embodiment of the present invention. A base end of the inner torsional spring 334 is coupled to the outer gimbal 320, and the opposite end of the inner torsional spring is coupled to the MEMS scanning mirror 310. The, composition, geometry and length of the inner torsional spring 334 are selected to achieve desired spring rates and other spring-related characteristics, as to be implemented with selected movement (e.g., frequency) of the MEMS scanning mirror 310.

FIG. 3C shows an outer vertical comb actuator (VCA) bank with corresponding spring arrangement for the MEMS arrangement shown in FIG. 3A (shown enlarged relative to that in FIG. 3A), according to another example embodiment of the present invention. A first end 351 of the outer torsional spring 350 is coupled to the outer base layer 370, and a second end 353 of the spring is coupled to the outer gimbal 320. As shown, the first end 351 of the outer torsional spring 350 is relatively wider than the second end 353. As discussed above in connection with the inner torsional spring 334 in FIG. 3B, the shape of the spring is thus selected to achieve a spring rate and/or other spring-related characteristics. For instance, the length of the relatively thicker end 351 of the outer torsional spring 350 can be selected relative to the total length of the outer torsional spring to achieve desired spring characteristics. That is, the thicker end 351 of the outer torsional spring provides a stiffer spring rate, relative to the relatively thinner end 353 of the outer torsional spring.

The VCA bank includes VCA arrays 340 and 342; each array includes comb-like structures extending along and adjacent to other comb-like structures, with an outer portion thereof coupled to the outer base layer 370 and with an inner portion thereof coupled to the inner gimbal 320. Referring to VCA array 342, an outer comb-like structure is labeled 343, and is immediately adjacent to an inner comb-like structure labeled 321. A multitude of similar comb-like structures are shown, making up each VCA array; the number, shape and composition of these structures are selected to suit particular scanning applications, with the example shown modifiable to suit these applications. A charge applied to the outer comb-like structures effects a force upon the inner comb-like structures and, accordingly, upon the inner gimbal 320, with the nature of the applied charge implemented to achieve various angles of rotation of the inner gimbal 320 and frequency of rotation.

As discussed above, the springs and VCA arrays shown with the MEMS arrangement 300 in FIGS. 3A, 3B and 3C can be implemented in a variety of manners, with different shapes, compositions and other characteristics selected to suit particular applications. For instance, while shown with two sets of torsional springs providing two dimensions of movement, the MEMS arrangement 300 in FIG. 3A can be selectively implemented with additional sets of torsional springs and corresponding VCA arrays to provide additional freedom in movement. For example, additional torsional springs and VCA arrays as shown in FIGS. 3B and 3C can be selectively implemented to provide additional manners in which movement of the MEMS scanning mirror 310.

In view of the above, the MEMS scanning arrangement 300 is amenable to implementation with a variety of approaches. In one application, the arrangement 300 is implemented with a tabletop two-photon microscope using the MEMS scanner. In some applications, the scanner is additionally equipped with a compound gradient refractive index (GRIN) microendoscope probe for two-photon endoscopy and may, for example, be implemented in a manner consistent with that shown in FIGS. 1A-2. For more information regarding such approaches, reference may be made to J. C. Jung, and M. J. Schnitzer, "Multiphoton endoscopy", Opt. Lett. 28, 902-905 (2003); and to M. J. Levene, D. A. Dombeck, K. A. Kasischke, R. P. Molloy, and W. W. Webb, "In vivo multiphoton microscopy of deep brain tissue." J. Neurophysiol 91, 1908-12 (2004); both of which are fully incorporated herein by reference.

In another implementation, a plurality of the MEMS scanning arrangements 300 are arranged immediately adjacent each other to form a MEMS scanning array, with each MEMS scanning mirror 310 of each scanning arrangement 300 controllable separably and/or in connection with the other MEMS scanning mirrors. Such an array may, for example, be implemented with the MEMS mirror arrangement 40 shown in FIG. 1A for a variety of applications, such as for in vivo scanning.

The arrangement 300 is further operable under a variety of conditions. In one application, the MEMS scanning mirror 310 is driven with sinusoidal voltage signals, and images are reconstructed based on calibration of the hysteretic, but repeatable, scan patterns. With this approach, specimens such as fluorescent pollen grains can be imaged using both two-photon microscopy and microendoscopy. Double-sided fast-axis acquisition rates are selectively implemented up to about 3.52 kHz. Micron-scale details of samples are selectively collected with such approaches.

FIG. 3D shows a MEMS scan unit 380 and mounting arrangement 390, according to another example embodiment of the present invention. The MEMS scan unit 380 may include, for example, a MEMS scanning arrangement 300 as shown in FIGS. 3A-3C. Furthermore, the MEMS scan unit 380 may include some or all of the items shown in FIGS. 1A-2, as referenced in various discussion above (e.g., with the items in a common scan unit arrangement), and coupled to the mounting arrangement 390.

In various applications, the overall dimensions of the mounting arrangement 390 represented by "H" and "W" are less than about 2 centimeters each. The mounting arrangement 390 is adaptable mounted to the head of a live being such as a mouse, and therein facilitates the positioning of the MEMS scan unit 380 relative to the live being under conditions wherein the live being is allowed to move freely. As discussed above prior to the discussion of the figures, the mounting arrangement 390 and scan unit 380 readily facilitate the observation of behavior of freely-moving beings while analyzing brain or other tissue over a period of time.

The characteristics shown in FIGS. 4 and 5 and described below may, for example, be implemented with the MEMS arrangement 300. In this regard, the following discussion makes reference to FIGS. 3A-3C (and is applicable to FIG. 3D); however, the various applications are applicable to a variety of MEMS arrangements as appropriate.

Figure 4:
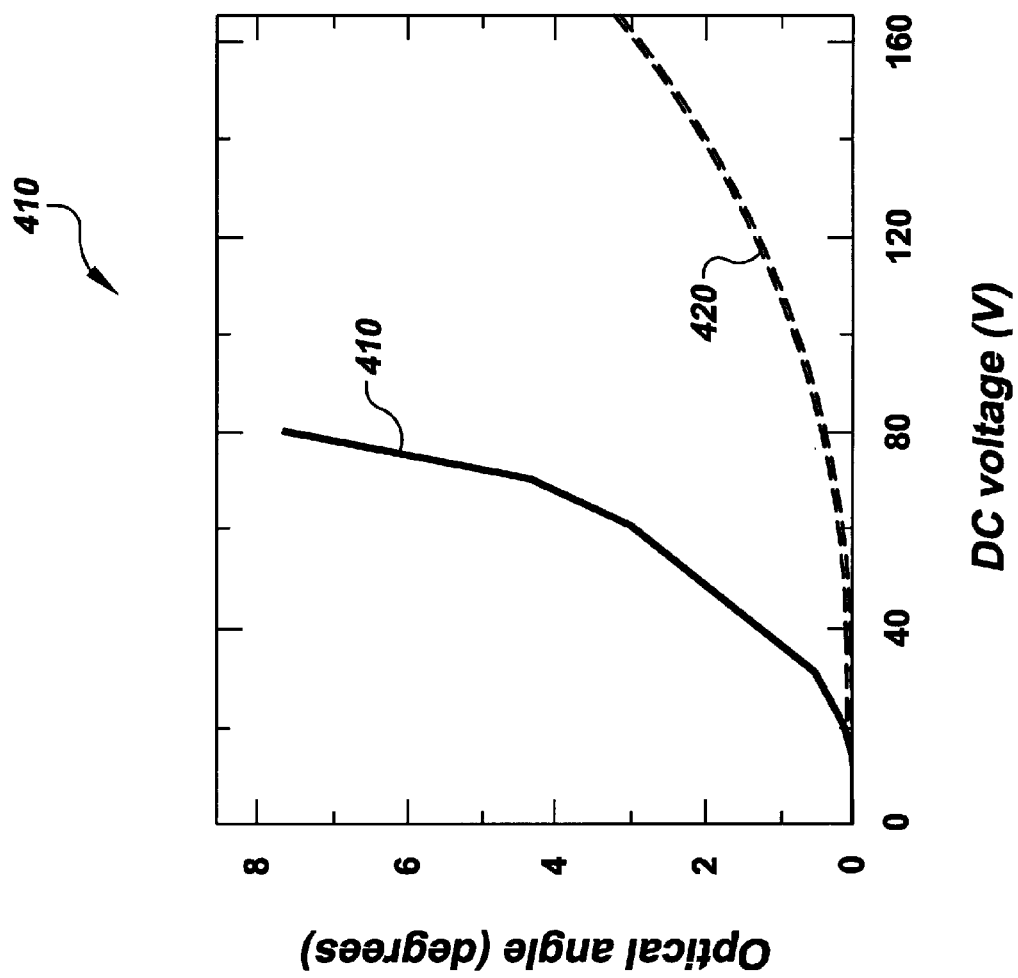
FIG. 4 shows DC transfer characteristics of a MEMS arrangement in accordance with another example embodiment of the present invention.

FIG. 4 shows DC transfer characteristics of a MEMS arrangement in accordance with another example embodiment of the present invention. Optical angle of a scanning MEMS mirror (and gimbal as appropriate) is shown in degrees on the vertical axis, and DC voltage applied to a VCA array or arrays is shown on the horizontal axis in volts. Plot 410 represents an inner axis, such as that corresponding to inner torsional springs 334 and 336, with achieved optical angles of ±7.6 degrees of rotation shown. Plot 420 represents an outer axis, such as that corresponding to outer torsional springs 350 and 352, with achieved optical angles of ±3.0 degrees of rotation shown.

Figure 5:
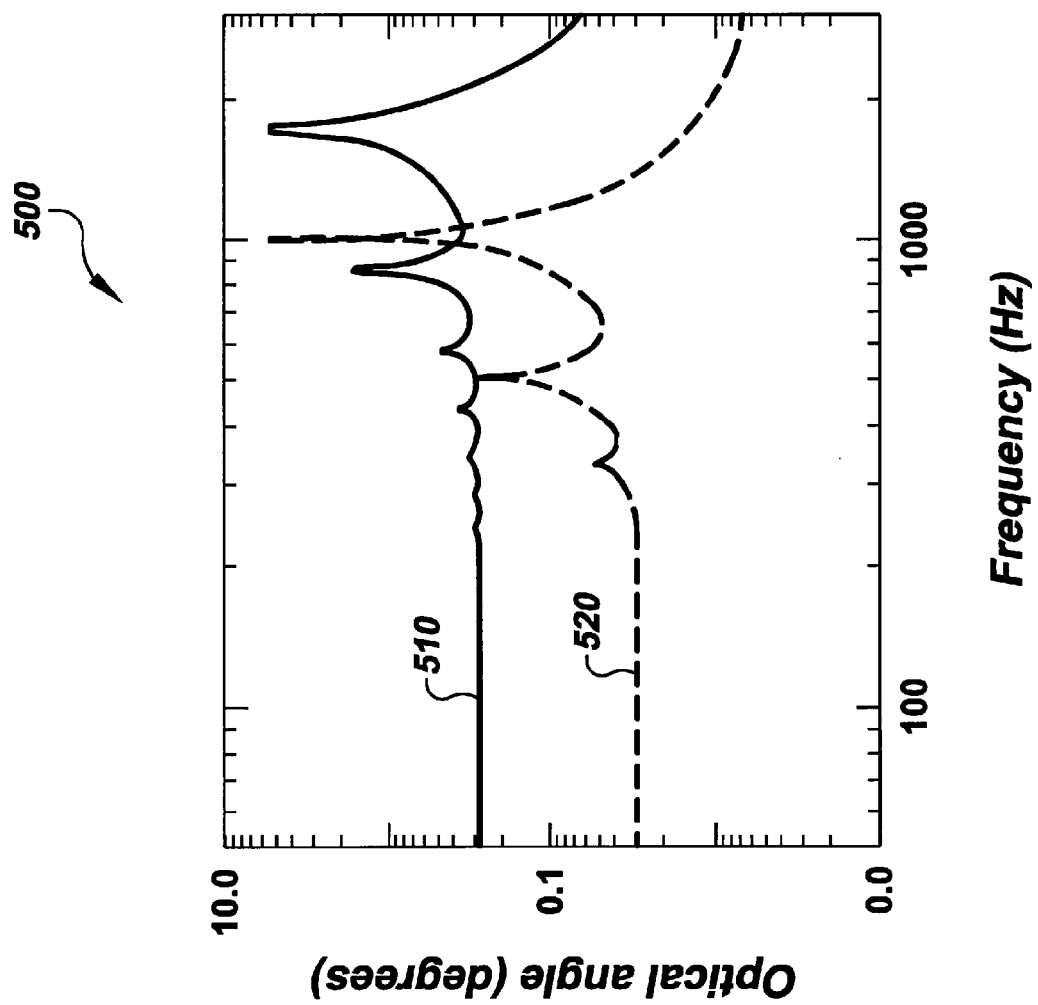
FIG. 5 shows frequency response functions for inner and outer axes of a MEMS arrangement such as that shown in FIG. 3A, according to another example embodiment of the present invention.

FIG. 5 shows frequency response functions for inner and outer axes of a MEMS arrangement such as that shown in FIG. 3A, according to another example embodiment of the present invention. As with FIG. 4, optical angle is shown on the vertical axis in degrees, with the horizontal axis being frequency (Hz) in this instance. Plot 510 represents the frequency response functions of an inner axis, such as that corresponding to inner torsional springs 334 and 336, with a primary resonant frequency of about 1.76 kHz shown. Plot 520 corresponds to an outer axis, such as that corresponding to outer torsional springs 350 and 352, with an achieved primary resonant frequency of about 1.09 kHz shown.

The approaches discussed above in general and in connection with the example figures are amenable to a variety of applications and further with selected approaches involving various devices, tools or other testing-type apparatus. In this regard, the following approaches are selectively implemented with one or more of the above examples, in connection with various example embodiments.

In one example embodiment, a lens implemented with a MEMS scanning analysis approach includes a correction lens that cancels optical aberrations. The lens is implemented in a manner similar to that shown, for example, with the GRIN objective 244 shown in FIG. 2. This approach facilitates near diffraction-limited resolution for in vivo imaging of fine biological structures discernible with visible light, such as neuronal dendritic spines, mitochondria and stereocilia.

In one embodiment directed to a GRIN lens approach, chromatic and wavefront aberrations present in GRIN micro-lenses are characterized and used to identify a corrective approach which is implemented with lenses used in obtaining an image from a sample. The wavelength dependence of the refractive index profile is numerically modeled, and initial measurements are made to ascertain variation of the on-axis index with wavelength. This approach facilitates modeling of the variation of the focal length of a GRIN objective lens over the visible spectrum. Custom correction lenses are then fabricated with the opposite chromatic dispersion tendencies of GRIN lenses, and facilitate the correction of chromatic and wavefront aberrations. Further, when selectively implemented with achromatic doublet lenses, the correction lenses facilitate the correction of spherical aberrations and coma to first order. Other applications involve triplet lenses. Calculations of spherical aberrations and coma take into account the aqueous environment and the working distance of the GRIN objective lens. These corrective lenses are implemented, for example, with the GRIN objective and/or Grin relay 244 and 242 shown in FIG. 2 (alone or with another lens arrangement).

In one example embodiment, correction lenses are implemented in a doublet arrangement with a crown glass convex lens of relatively low refractive index and dispersion combined with a flint glass concave lens of relatively higher index and dispersion. If $f_1$, $f_2$ and $V_1$, $V_2$ are the respective lens focal lengths and Abbe numbers (a measure of chromatic dispersion), then the Abbe condition for having the same focal length at the top and bottom of the spectral range is $f_1V_1+f_2V_2=0$. This approach can be facilitated by a doublet that has a plano-convex shape, and which thus suffers minimally from spherical aberration and coma. The Abbe condition of the doublet arrangement is modified so $f_1V_1+f_2V_2$ is not zero, balancing the chromatic aberrations from our GRIN micro-lenses. In some applications, this modification of the Abbe condition is facilitated via choice of lens materials, rather than alteration of the doublet's shape, inhibiting spherical aberrations. In some applications, separate correction lenses are implemented for one- and two-photon imaging approaches, since the relevant spectral ranges for the different approaches are quite distinct. In one implementation, a relay correction lens is combined with an objective correction lens to facilitate correction.

One example imaging technique that may be used in connection with one or more example embodiments discussed herein involves laser scanning fluorescence microscopy using, for example, one or more of the arrangements shown in FIG. 1A, 1B or 2, and in some applications, a MEMS arrangement as shown in FIG. 3A. Focused laser light is scanned across a sample using a MEMS mirror such as the MEMS scanning mirror 310 in FIG. 3, actuated via the inner and outer VCA arrays and along axes defined by inner torsional springs 334 and 336, and by outer torsional springs 350 and 352. The MEMS scanning mirror 310 may, for example, be implemented with an approach that can be characterized by the plots shown in FIGS. 4 and 5, to achieve the laser scanning as discussed above.

Fluorescent probes inside of the sample absorb the laser light and emit fluorescence at a different wavelength. The fluorescence light is collected and used to visualize the sample. In some applications, this approach is implemented to facilitate sectioning; that is, the sample may be visualized sub-surface and at varying depth profiles, with stimulation and response light passed via a lens at an embedded end of a capillary. In addition, fluorescent probes may be attached to a structure of interest inside of a biological sample such as a protein, a drug, a sequence of DNA, an RNA sequence or a selected molecule. Laser scanning fluorescence microscopy then allows for visualization of the distribution of said structure of interest.

In some applications, laser scanning fluorescence microscopy is combined with a nonlinear optical process such as two-photon absorption, typically referred to as two-photon fluorescence microscopy or two-photon laser-scanning fluorescence microscopy. When a two-photon approach is implemented with an in vivo application, a fluorescent probe inside of the sample (i.e., at a location below the implanted end of a capillary) absorbs two-photons from a laser pulse that uses short pulses or pulses in the femtosecond to picosecond range and emits a fluorescence photon at a lower wavelength.

This approach is generally beneficial in reducing photobleaching and phototoxicity, relative to other conventional approaches, and is generally robust to light-scattering inside of the sample.

Other nonlinear optical processes used in connection with various examples visualize surface and sub-surface structures inside of a sample via laser-scanning of a sample with one or multiple lasers (i.e., as directed by a MEMS mirror). In one instance, a harmonic generation approach such as second-harmonic generation (SHG) or third harmonic generation (THG) is used to generate a nonlinear response that is detected and used to garner information about a sample. In other instances, nonlinear processes such as Raman scattering or Raman spectroscopy, or Coherent Anti-Stokes Raman Scattering (CARS) are used in stimulating and analyzing sample.

In the above and other example embodiments of the present invention, various characteristics of light direction approaches (such as those involving a MEMS mirror implementation and/or associated optical arrangements) are directed to specific functions relating to the stimulation of and/or detection of nonlinear optical characteristics in a sample. In this regard, certain characteristics of the above approaches and those shown in the Figures are selectively tailored for nonlinear type conditions.

In various example embodiments, a nonlinear optical detection system such as that discussed above further includes implantable stimulation-facilitating devices that are implanted in a specimen, such as shown in FIGS. 1A-2. One application involves the use of a system including a light source, MEMS mirror (e.g., MEMS scanning mirror 310), fluorescence probes (for implantation with a sample) and a wavelength-dependent light collection apparatus. The fluorescence probes are configured to interact with light from the source scanned to the probes by the MEMS mirror, and to facilitate a nonlinear response of the sample in which the probes are implanted. This response includes light that is passed to a detector (e.g., detector 230 in FIG. 2) characterized in that the wavelength of the light is different than the wavelength of the source light. Other nonlinear optical detection applications involve the use of devices separate from or in addition to the fluorescence probes, with such devices similarly facilitating the generation of a detectable nonlinear optical response of the sample. These other applications may include, for example, harmonic generation applications, Raman scattering applications or Coherent Anti-Stokes Raman Spectroscopy (CARS) applications, e.g., as discussed above.

For general information regarding optical analysis and for specific information regarding approaches to analysis that may be implemented in connection with one or more example embodiments herein, reference may be made to the following patent documents: U.S. Pat. Nos. 6,485,413 and 6,423,956, and U.S. Patent Application Publication Number US 2003/0142934; each of these is fully incorporated herein by reference. For example, the mirrors implemented in one or more of these example patent documents may be implemented in connection with various example embodiments discussed herein. One or more different types of light sources are implemented, depending upon the application and availability. In some applications, more than one light direction and/or collection arrangement is used to provide additional functionality. Moreover, some or all of the example embodiments and implementations herein are selectively combined with approaches to the analysis of live beings, with a combination of behavior observation of a live being in a freely-moving state with observation of tissue within the live being. These live-being analysis approaches are facilitated by the size, weight, arrangement and/or control of the various analysis devices discussed herein.

While the present invention has been described with reference to several particular example embodiments, those skilled in the art will recognize that many changes, including those discussed in the preceding paragraph, may be made thereto without departing from the spirit and scope of the present invention.

What is claimed is:

1. An optical system for analyzing a live being, the system comprising:
   a light source;
   a light direction arrangement adapted to be physically secured to a live being, the light direction arrangement including
      a micro-mirror,
      an actuator for controllably moving the micro-mirror to direct light from the light source to different target locations of the live being, and
      a dichroic device to direct light directed from the light source via the micro-mirror to the live being and to direct light from the live being to a light detector; and
   a light detector configured and arranged to receive and detect light from the live being, via the dichroic device, and to present a signal characterizing the detected light.

2. The system of claim 1, further including a fastener to secure the light direction arrangement to the live being to maintain a spatial relationship between the micro-mirror, the dichroic device and the different target locations of the live being.

3. The system of claim 2, wherein the fastener fastens the light direction arrangement to tissue of the live being, wherein the actuator is adapted to controllably move the micro-mirror to direct light to the different target locations of the live being while the live being moves in an unanesthetized state, the fasteners maintaining a spatial relationship between the micro-mirror and the live being to facilitate the light direction while the live being moves.

4. The system of claim 1, wherein at least one of the light source and the light detector are secured to the light direction arrangement.

5. The system of claim 1, wherein the light direction arrangement is configured and arranged to facilitate the detection of a nonlinear optical response from the live being, the nonlinear optical response being generated in response to the directed light from the light source.

6. The system of claim 5, wherein the light direction arrangement is configured and arranged to generate a nonlinear optical response in the live being by stimulating a portion of the live being adapted to facilitate a nonlinear optical response.

7. The system of claim 1, wherein the light direction arrangement is configured and arranged to facilitate the detection of a linear optical response from the live being, the linear optical response being generated in response to the directed light from the light source.

8. The system of claim 1, further comprising a capillary implanted into the live being, wherein at least the micro mirror of the light direction arrangement are inserted in the capillary for directing light from the light source to the different target locations of the live being.

9. The system of claim 8, wherein the light direction arrangement is adapted to scan light from the light source across a target area at a subcutaneous portion of the live being, the dichroic device adapted to direct light from the target area to the light detector.

10. The system of claim 1, wherein the micro-mirror is fabricated on a single-crystalline silicon wafer.

11. The system of claim 1, wherein the actuator includes a vertical comb actuator array responsive to a voltage by rotating the micro-mirror about an axis.

12. The system of claim 11, wherein the vertical comb actuator array is responsive to an applied sinusoidal voltage to rotate the micro-mirror about an axis at a frequency of at least about 1.5 kHz.

13. The system of claim 1, wherein the micro-mirror is attached to two sets of springs, each set of springs lying along a common axis about which the micro-mirror rotates via the set of springs, and wherein the actuator includes at least one vertical comb actuator for each set of springs and adapted to rotate the micro-mirror about an axis along which the set of springs lies, further comprising a controller adapted to control the vertical comb actuators for controlling the micro-mirror to scan light from the light source across a target location in the live being.

14. The system of claim 13, wherein the controller is adapted to apply a sinusoidal voltage to the vertical comb actuators to control the micro-mirror to scan light from the light source at a selected frequency.

15. The system of claim 1, wherein the light source includes at least two light sources.

16. The system of claim 1, further comprising a plurality of said light direction arrangements in an array and adapted to scan light from a light source to target locations in the live being.

17. The system of claim 16, wherein the light detector is adapted to detect light emitted from the target locations in response to each of the light direction arrangements.

18. The system of claim 1, wherein the dichroic device separates different wavelengths for generating a multi-channel image and wherein the light detector uses the different wavelengths to generate a signal characterizing the multi-channel image.

19. The system of claim 1, wherein the light source is a laser that generates light having a wavelength that stimulates the emission of photons from the target locations to facilitate two-photon imaging of the target locations.

20. The system of claim 1, wherein the light direction arrangement includes a microscope adapted to detect emitted photons in a two-photon microscopy approach.

21. An optical system for analyzing live beings in an unanesthetized state, the system comprising:
a base fastened to a live being;
a laser light source adapted to generate pulses of laser light for stimulating tissue in the live being;
a light direction arrangement coupled to the base and comprising
a micro-mirror adapted to controllably rotate about at least two axes, and
an actuator for controllably moving the micro-mirror to scan light from the light source across different target locations of subcutaneous tissue of the live being to stimulate a fluorescent response of the subcutaneous tissue, and
the base adapted to maintain a spatial relationship between the micro-mirror and the subcutaneous tissue of the live being while the live being moves;
a light detector that detects photons emitted from the subcutaneous tissue as part of the fluorescent response and presents a signal characterizing the detected photons; and
a computer arrangement that receives the signal from the light detector and uses the signal to present information for use in characterizing a condition of the live being.

22. The system of claim 21, wherein at least one of the light source and the light detector is coupled to the base.

23. The system of claim 21, wherein the base and light direction arrangement have a combined weight of less than about 3 grams.

24. The system of claim 21, wherein the light detector is coupled to the base and adapted to pass a wireless signal characterizing the detected light to a computer arrangement.

25. The system of claim 21, further comprising a power supply coupled to the base and adapted to power at least one of the actuator, the laser light source and the light detector.

26. A method for analyzing a live being, the method comprising:
fastening a light direction arrangement to a live being, the light direction arrangement including a micro-mirror, an actuator for controllably moving the micro-mirror to direct light from the light source to different target locations of the live being, and a dichroic device configured and arranged to direct light from the live being to a light detector;
allowing the live being to move freely with the light direction arrangement fastened thereto; and
while the live being is allowed to move freely,
directing light to the micro-mirror arrangement,
applying a voltage to the actuator to cause the micro-mirror to oscillate and thereby scanning light to subcutaneous tissue of the live being via the dichroic device, and
detecting a response of the subcutaneous tissue to the scanning via light directed by the dichroic device.

27. The method of claim 26, further comprising observing the live being over time while concurrently detecting a response of the subcutaneous tissue to the scanning.

* * * * *